United States Patent [19]

Jessop et al.

[11] 4,272,482

[45] Jun. 9, 1981

[54] METERING APPARATUS

[75] Inventors: Thomas C. Jessop, Webster; Jeffrey L. Helfer, Rochester, both of N.Y.

[73] Assignee: Eastman Kodak Company, Rochester, N.Y.

[21] Appl. No.: 54,060

[22] Filed: Jul. 2, 1979

[51] Int. Cl.³ .................... G01N 35/04; G01N 35/06
[52] U.S. Cl. .................................. 422/65; 73/864.25; 141/130; 422/66; 422/100
[58] Field of Search .............. 422/63, 64, 65, 66, 422/67, 100, 103; 141/130; 73/425.6, 425.4 R

[56] References Cited

U.S. PATENT DOCUMENTS

| | | |
|---|---|---|
| 3,150,001 | 9/1964 | Hrdina . |
| 3,168,124 | 2/1965 | Lenkey . |
| 3,181,574 | 5/1965 | Lenkey et al. ............... 141/130 |
| 3,189,413 | 6/1965 | Davis . |
| 3,239,312 | 3/1966 | Bell et al. . |
| 3,428,547 | 2/1969 | Zec . |
| 3,542,093 | 11/1970 | Pollmann ................. 141/130 |
| 3,576,605 | 4/1971 | Drake et al. . |
| 3,623,515 | 11/1971 | Gilson ...................... 141/130 |
| 3,683,977 | 8/1972 | Crowe et al. ............. 141/130 |
| 3,687,632 | 8/1972 | Natelson . |
| 3,833,341 | 9/1974 | Tocci ........................ 141/130 |
| 3,992,158 | 11/1976 | Przybylowicz et al. ...... 422/57 |
| 4,053,381 | 10/1977 | Hamblen ................. 204/195 M |
| 4,152,390 | 1/1979 | Nosco ........................... 422/63 |

*Primary Examiner*—Ronald Serwin
*Attorney, Agent, or Firm*—Donald D. Schaper

[57] ABSTRACT

Apparatus is disclosed which is adapted to repeatedly and accurately dispense predetermined amounts of fluid, especially biological fluids, onto generally planar test elements. The apparatus comprises a movable carriage for supporting and locating a dispensing device at a plurality of metering stations in an analyzer. A pair of locating means are operable in sequence to precisely locate the dispensing device relative to a test element in each of the stations.

15 Claims, 7 Drawing Figures

METERING APPARATUS

BACKGROUND OF THE INVENTION

1. Field of the Invention

This invention relates to the chemical analysis of substances, and more particularly, to apparatus for supporting and locating a dispensing device in a plurality of stations of a chemical analyzer.

2. State of the Prior Art

A number of automated systems have been developed for performing quantitative chemical analysis of fluid samples. Most of the commercially-available systems utilize liquid reagents and require analyzer equipment having intricate solutions handling and transport capabilities. Recent developments, however, have provided test elements in essentially planar, dry form which can be loaded into a cartridge for use in an analyzer. In the use of such an analyzer, a test element from a cartridge is fed into a metering station where a predetermined amount of sample fluid is deposited on the test element. After an incubation period, a change in the test element is measured at an analysis station, the amount of change being proportional to a particular analyte in the fluid. The test element is used only once and is discarded after the reading has been taken. An analyzer for use with such test elements is disclosed in commonly-assigned U.S. Pat. No. 4,152,390, granted May 1, 1979.

Test elements of the type described above are adapted to function with very small quantities of fluid. For example, test elements for performing colorimetric analyses can produce a measurable response with only ten microliters of sample fluid, and elements for performing potentiometric analyses are operable with ten microliters of sample fluid and ten microliters of reference fluid. Very precise metering devices are required for use with such test elements, since the volume of fluids supplied to the elements should preferably not vary more than five percent (5%) from a selected value to achieve desirable test results. Further, the metering tips through which the fluids are expelled onto the test elements must be precisely located relatively to the elements to obtain accurate test results.

In liquid dispensing systems, it is known to mount a dispensing device on a movable carriage such that the device can be indexed to a plurality of dispensing sites. In the patent to Lenkey, U.S. Pat. No. 3,168,124, granted Feb. 2, 1965, a fluid delivery unit, for dispensing fluids into an array of test tubes, is mounted on a register bar and is advanced past the test tubes by a motor-driven lead screw. Abutments are provided on the register bar and a detent member is adapted to position the dispensing unit at each abutment. Since the apparatus disclosed in the Lenky Patent is used for delivering fluid to a relatively large opening in a test tube, there is no provision for precisely locating the dispensing unit relative to a substrate.

Relatively small, portable analyzers have been developed for use with the generally planar test elements described above. Such analyzers are used in operating rooms for emergency tests, or carried in ambulances for field use. Preferably these analyzers should be simple and manually actuated, since power may not be available. Known metering apparatus for analyzers of this type, however, lack the precision required for acceptable results, and are not suitable for use in multichannel analyzers.

OBJECTS OF THE INVENTION

It is the object of the present invention to overcome the above-described problems in prior-art devices, and to provide a novel and improved metering apparatus for use with relatively simple, small analyzers.

It is another object of the invention to provide metering apparatus in which a pair of locating means are operable in sequence to precisely locate a dispensing device relative to a substrate.

Still another object of the invention is to provide means for moving a dispensing device to a plurality of stations in an analyzer and for precisely locating the device in each of said stations.

Yet another object of the invention is to provide a means for locking a dispensing device in position during the dispensing of fluids onto a substrate.

A further object of the invention is to provide a carriage, for supporting a dispensing device, which is movable to a plurality of stations in an analyzer and is movable from a transport position to a dispense position in each of the stations.

Other objects and advantages will become apparent from the following summary and description of the preferred embodiments, when considered in the light of the attached drawings.

SUMMARY OF THE INVENTION

This invention relates to metering apparatus for repetitive, precise dispensing of a microquantities of sample fluids onto a substrate in the form of a generally planar test element. More specifically, the invention relates to apparatus for supporting and locating a dispensing device at a plurality of stations in a chemical analyzer.

In accordance with one aspect of the invention, there is provided apparatus for depositing a predetermined amount of fluid on a test element at a plurality of metering stations in a chemical analyzer, the apparatus comprising: means for dispensing fluid in precise amounts and for aspirating a supply of fluid from a sample cup; carriage means for supporting the dispensing and aspirating means for movement to each of the stations; support means for the carriage means, the support means extending along each of the stations; and means for positioning the carriage means at each of the stations, the positioning means comprising a first location means for locating the carriage means between predetermined limits and second locating means for locating the carriage means within said limits relative to a test element in a metering station.

In one embodiment of the invention, a metering apparatus comprises a carriage which is mounted for longitudinal and pivotal movement on a shaft which extends along the rear of the analyzer. The carriage comprises a generally horizontally extending support arm which carries the dispensing means, and a detent arm which is fixed to the support arm at an upper end and is generally perpendicular thereto. The detent arm has a roller at its lower end which is mounted for movement in a track. A vertically extending counterbalance arm is also mounted on the shaft and carries a roller at one end which is adapted to move in a track adjacent the track which carries the roller on the detent arm. A spring connects the detent arm and the counterbalance arm and serves to bias the carriage into a transport position.

Positioning means are provided at each of the stations in the analyzer for locating the dispensing means relative to a test element. The positioning means comprises a first locating means in the form of detent slots in the track which carries the roller on the detent arm; the detent slots locate the dispensing means within predetermined limits and also permit the carriage to pivot from a transport position to a dispense position. As the carriage approaches the dispense position, a second locating means, more precise than the first locating means, locates the dispensing means in a horizontal plane relative to a test element and spaces the dispensing means from the test element in a vertical direction.

DESCRIPTION OF THE PREFERRED EMBODIMENT

The invention is described hereinafter in connection with an analyzer for performing quantitative chemical analyses of biological fluids, such as blood serum. However, the invention is not so limited and it can be employed in other types of apparatus where dispensing devices must be precisely located relative to a substrate.

The invention is particularly useful with potentiometric analyzers in which case the substrate which makes the test possible comprises a pair of electrodes selective to the ion activity of choice. Recent developments have provided the electrodes in essentially planar, dry form suitable for use in pairs in an analyzer. Such an analyzer is described and claimed in U.S. patent application Ser. No. 927,702, entitled CHEMICAL ANALYZER, and filed in the name of Schnipelsky, on July 24, 1978. The invention can also be employed in an analyzer using a radiometric detector which will read a suitable substrate incorporating, for example, reagents that create a dye in proportion to the analyte being measured. An analyzer of this type is disclosed in the aforesaid commonly-assigned U.S. Pat. No. 4,152,390.

One form of test element for use with the apparatus of the subject invention is disclosed in the patent to Hamblen, U.S. Pat. No. 4,053,381, granted on Oct. 11, 1977. This patent describes a test element, or analysis slide, of the type which potentiometrically designates the activity of ions in a liquid test solution by the use of electrodes. The invention can also be used with other forms of test elements as, for example, the element disclosed in the commonly-assigned U.S. patent to Przybylowicz et al., U.S. Pat. No. 3,992,158, granted on Nov. 16, 1976. The test element disclosed in this patent is formed as a multi-layer element containing the necessary reagents for reaction with components of a biological fluid, such as blood serum, deposited thereon. Certain reactions colorimetrically produce a change in optical density in the element which is sensed by a reflectometer, the amount of light reflected from the element varying at the accordance with the reaction and being indicative of the amount of a particular analyte present in the fluid.

Figure 1:
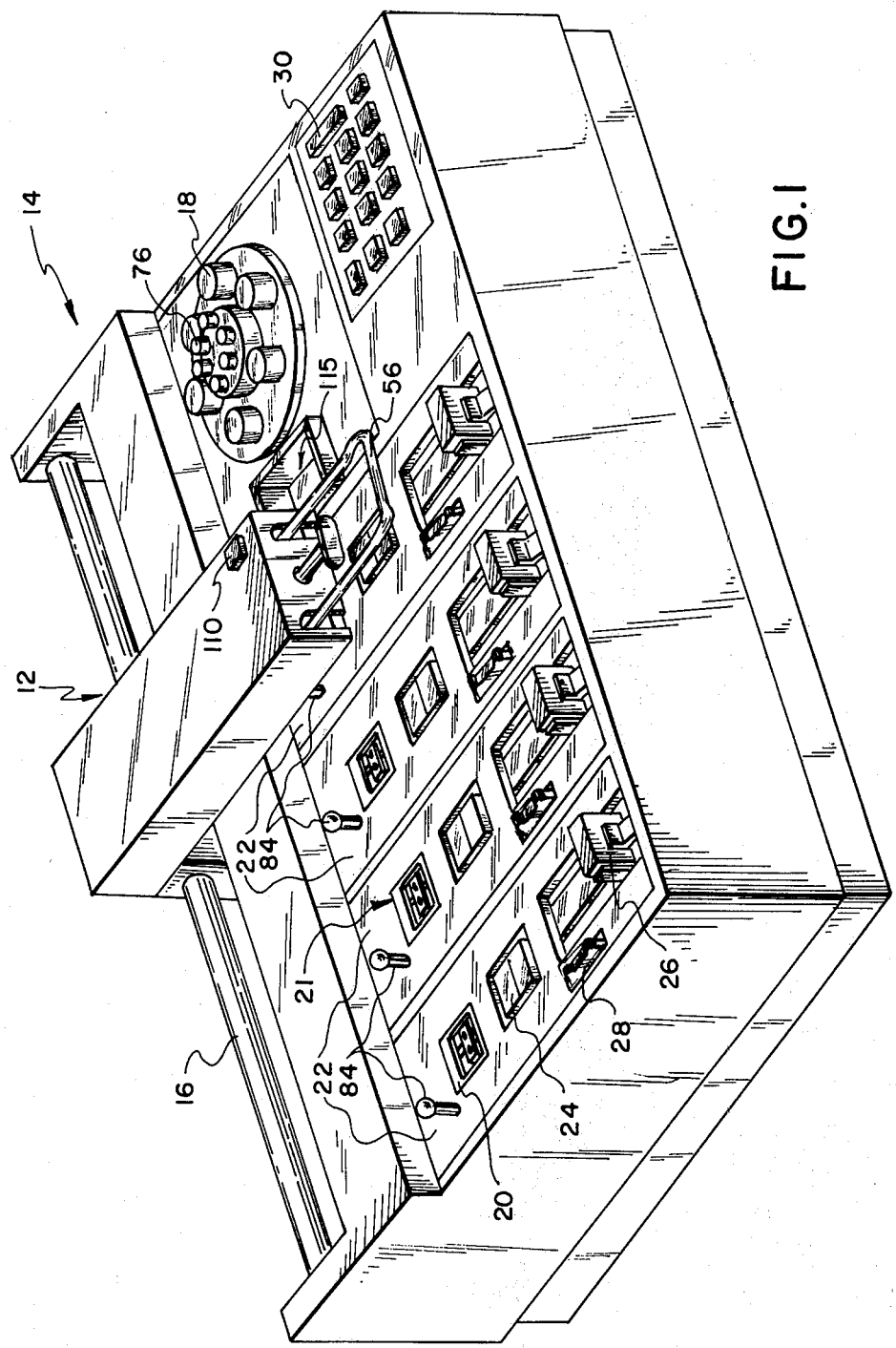
FIG. 1 is a perspective view of a chemical analyzer of the type which is adapted to employ the metering apparatus described herein.
Figure 2:
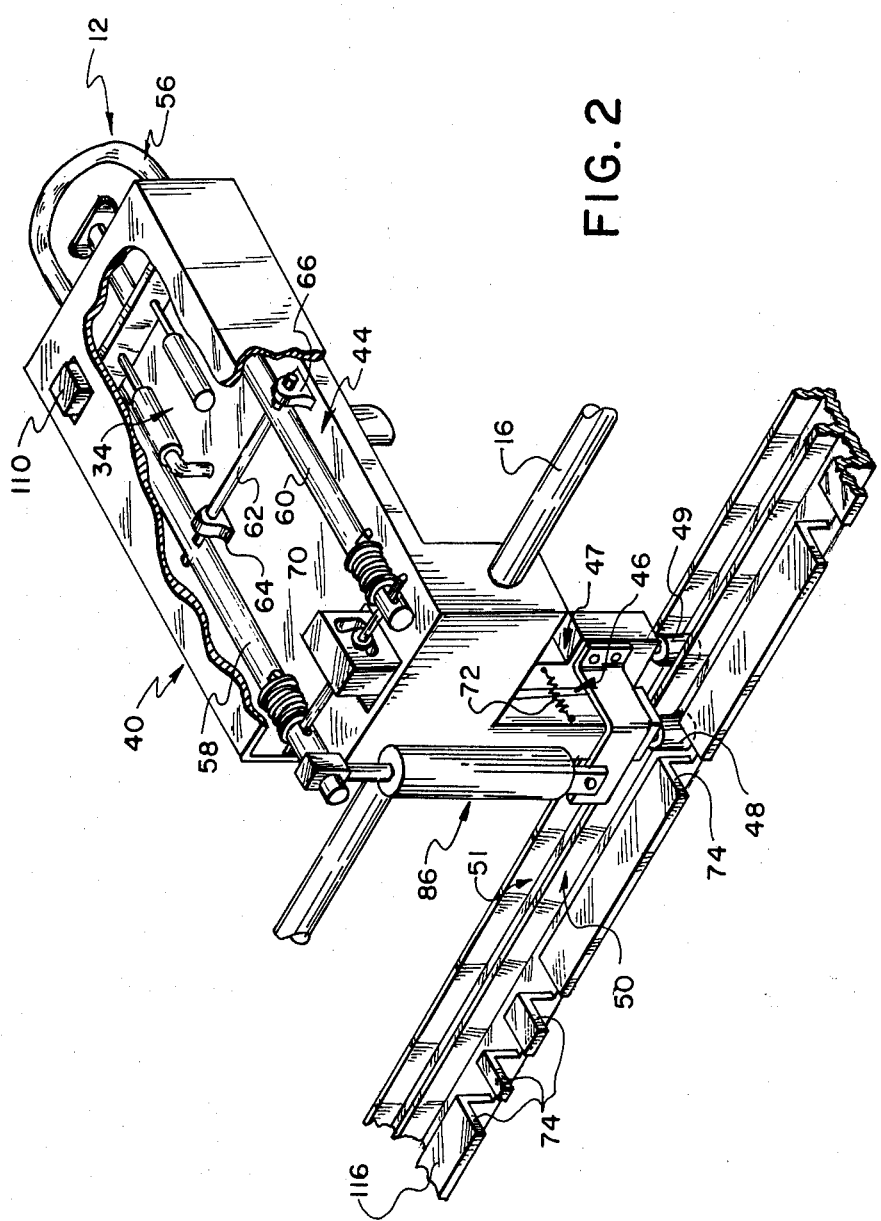
FIG. 2 is a perspective view of the metering apparatus of the subject invention, with parts broken away to show elements of the carriage and the dispensing means.

In accordance with a preferred embodiment of the invention, there is shown in FIG. 2 a metering apparatus 12 constructed in accordance with the invention. Metering apparatus 12 is adapted to be used in a multi-channel potentiometric analyzer 14 of the type shown in FIG. 1. With reference to FIG. 1, the analyzer 14 comprises a shaft 16, located along the rear of the analyzer, which is adapted to support metering apparatus 12 for movement in analyzer 14. Metering apparatus 12 is adapted to draw in, or aspirate, a supply of sample fluid from a cup 18; the apparatus 12 is then moved along shaft 16 to a metering station 21 in a channel 22 of analyzer 14. When the metering apparatus 12 is located at a metering station 21, the apparatus 12 is pivoted down into a dispense position directly over a test element 20 where it substantially simultaneously deposits a predetermined quantity of sample fluid and a predetermined quantity of reference fluid onto the test element 20. After an incubation period, a potentiometric reading of the test element 20 is taken by an electrometer, not shown.

As shown in FIG. 1, analyzer 14 comprises four channels 22; metering apparatus 12 is adapted to successively dispense fluid onto an element 20 in each of the channels 22. Test elements 20 are supplied to analyzer 14 in cartridges 24, and the elements 20 are sequentially fed from the cartridges and advanced through the analyzer by means of a slide transfer mechanism 26. A control knob 28 is used to program the analyzer 14 for the desired test, as disclosed in U.S. patent application Ser. No. 37,250, entitled CHEMICAL APPARATUS, filed in the name of Jessop, on May 9, 1979. A keyboard 30 is used by the operator to provide input data to analyzer 14.

Metering apparatus 12 must be capable of repeatedly and accurately dispensing very small quantities of fluid; for example, test element 20 (FIG. 1) which is of the potentiometric type can produce a measurable response with only ten microliters of reference fluid and ten microliters of sample fluid. As shown in FIG. 2, metering apparatus 12 comprises a dispensing device 34 which is adapted to aspirate sample fluid into the dispensing means 34, and to substantially simultaneously dispense a predetermined quantity of reference fluid and of sample fluid onto a test element 20, as disclosed in U.S. patent application Ser. No. 054,064, entitled METERING APPARATUS, filed in the name of Jessop et al., on even date herewith. Dispensing device 34 is supported on a carriage 40 which is journalled on shaft 16 for longitudinal and for pivotal movement.

Figure 3:
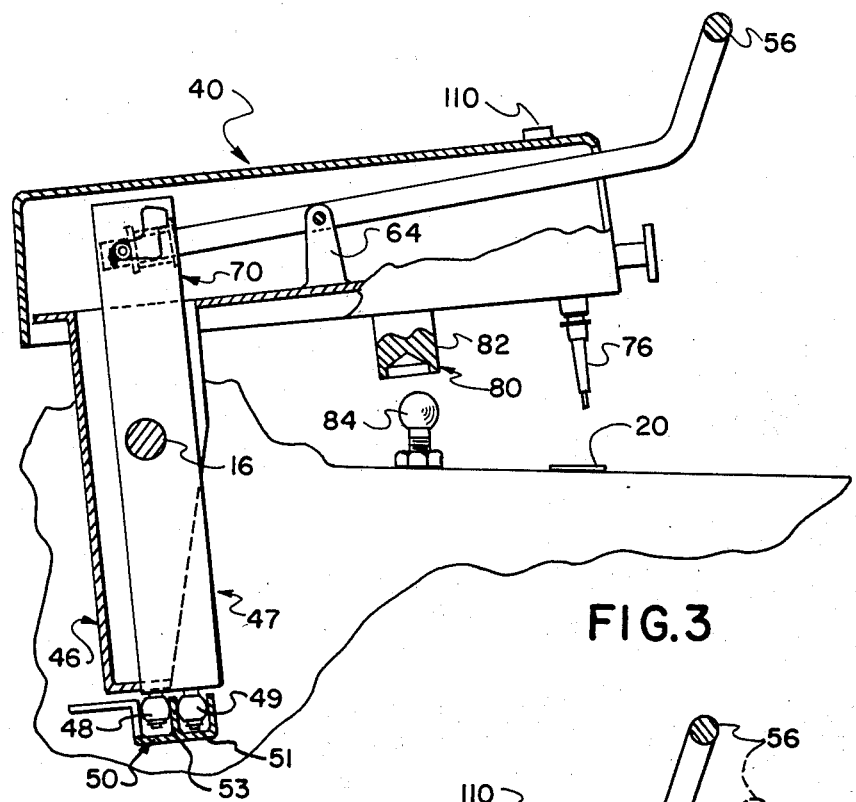
FIG. 3 is a side elevational view, shown partially in section, of the metering apparatus and showing the carriage in the transport position.

Carriage 40 comprises a support arm 44 which is adapted to receive dispensing means 34, a detent arm 46, and a counterbalance arm 47. When analyzer 14 is in its normal position for operation, support arm 44 extends generally horizontally and detent arm 46 and counterbalance arm 47 extend generally vertically. Carriage 40 is movable along shaft 16 from station to station in a transport position, as shown in FIG. 3. The carriage 40 is maintained in the transport position by means of a roller 48 affixed to detent arm 46 and a roller 49 carried on counterbalance arm 47. Rollers 48, 49, are mounted respectively in tracks 50, 51. As shown in FIG. 3 tracks 50, 51, have a common wall 53, and rollers 50, 51 are biased toward wall 53 by a spring 72 which is attached to detent arm 46 and counterbalance arm 47.

A handle 56 is provided for moving carriage 40 along shaft 16 to successively position dispensing device 34 in the metering stations 21 of the four channels 22, and for pivotally moving the carriage 40 from a transport position to a dispensing position, as will be explained in more detail hereinafter. Handle 56 is generally U-shaped and comprises a pair of members 58, 60, which are connected to a pin 62 journalled in supports 64, 66. Members 58, 60, are also connected to a position lock 70, best shown in FIGS. 6 and 7, which is adapted to releasably hold carriage 40 in a dispense position.

Figure 4:
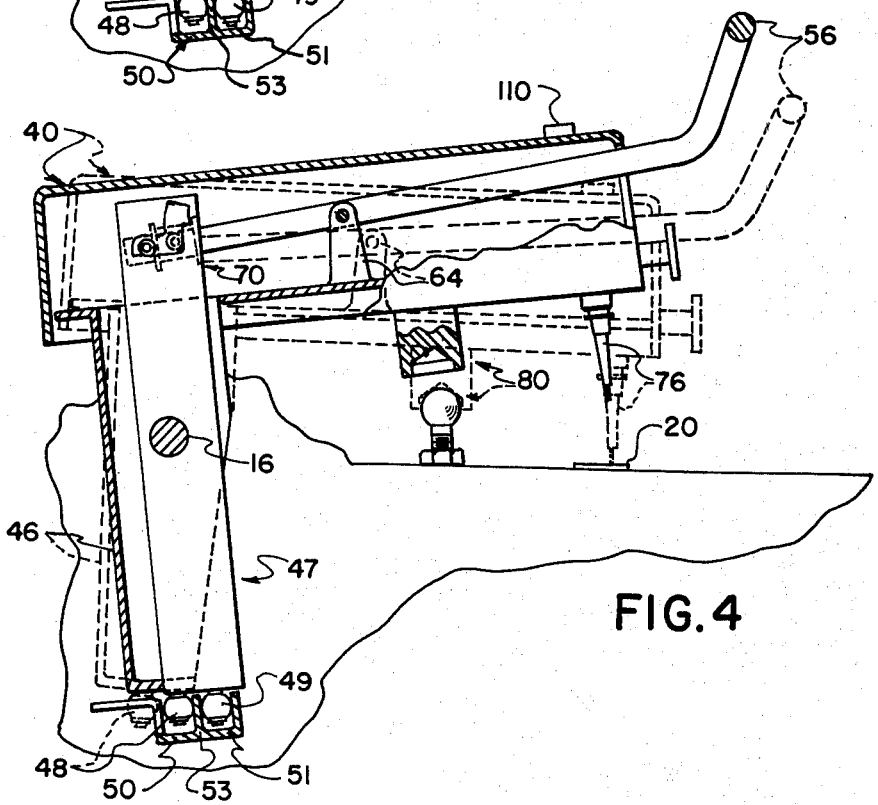
FIG. 4 is a side elevational view, shown partially in section, of the metering apparatus and showing the carriage in the transport position in solid lines and in the dispense position in dotted lines.

Carriage 40 is adapted to pivot from a transport position, shown in solid lines in FIG. 4, to a dispense position shown in dotted lines in FIG. 4, at each of the channels 22 in analyzer 14. A detent slot 74, provided in track 50 adjacent each of the channels 22, is adapted to receive roller 48 on arm 46. In normal operation, the operator would apply a slight downward force on handle 56 as carriage 40 is moved along shaft 16; thus, when roller 48 contacts a slot 74, the roller would drop into the slot to stop the carriage and to signal the operator that the carriage was located at a particular channel. The operator can, of course, choose to by-pass a channel by applying no downward force, or a slight upward force, to maintain the carriage in the transport position. Detent slot 74 serves as a first locating means to locate dispensing device 34 relative to a test element 20 between predetermined limits at a selected channel 22. To start the metering operation, the operator presses down on carriage handle 56 which moves detent roller 48 further into slot 74; this downward movement, against the bias of spring 72, pivots carriage 40 in a clockwise direction, as viewed in FIG. 3, and moves a metering tip 76 toward a test element 20.

Figure 5:
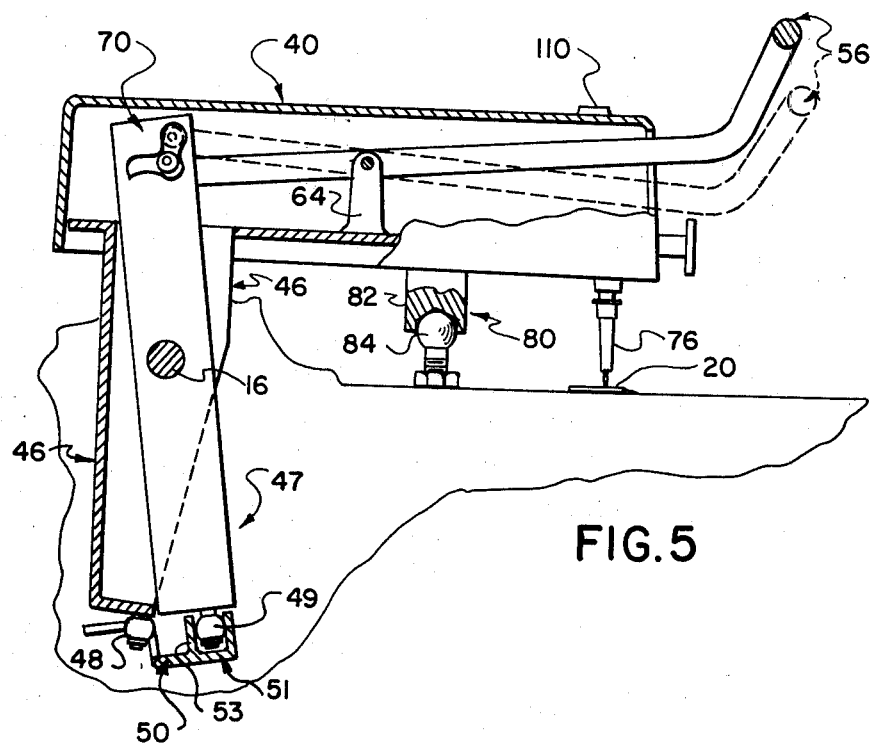
FIG. 5 is a side elevational view, shown partially in section, of the metering apparatus and showing the position of the handle in solid lines at the point where the carriage has just moved into the dispense position and in dotted lines when the carriage is locked into the dispense position.

As tip 76 approaches the test element 20, a second locating means 80 is operable on carriage 40 to precisely locate tip 76 relative to element 20. (See FIGS. 3-5). Locating means 80 comprises a socket 82 affixed to suport arm 44, and a ball 84 which is adapted to be received in socket 82, as shown in FIG. 5. Locating means 80 serves to precisely locate tip 76 relative to element 20 within the limits established by detent slot 74, in a horizontal plane, and also controls the vertical spacing between tip 76 and element 20.

It will be apparent to those skilled in the art that the second locating means 80 could include means operable directly on tip 76 in lieu of, or in combination with, the ball 84 and socket 82. For example, a member having a tapered bore could be located just above a test element 20 in the metering station; as carriage 40 is moved into the dispensing position, tip 76 would be received in the bore and guided by the walls of the bore to the desired location, in a horizontal plane, relative to the test element 20. It would also be possible to locate the tip vertically by providing structure around the bore which cooperates with a shoulder on tip 76; in such an arrangement it may be desirable to provide for limited vertical movement of tip 76 against a spring or other biasing means. Although only one metering tip 76 is shown in FIGS. 3-5, it will be understood that, for test elements 20 of the potentiometric type, a second metering tip is required for dispensing reference fluid, as disclosed in the aforementioned U.S. patent application Ser. No. 054,064, entitled METERING APPARATUS.

A dash pot 86 is connected between counterbalance arm 47 and support arm 44 to control the rate at which carriage 40 is pivoted into the dispense position, thereby avoiding the possibility that fluid will be ejected from tip 76 by a fast pivotal movement of carriage 40. Dash pot 86 also controls the withdrawal rate of tip 76 from a sample cup 18, after aspiration, to minimize the amount of fluid which adheres to the exterior of tip 76.

Figure 6:
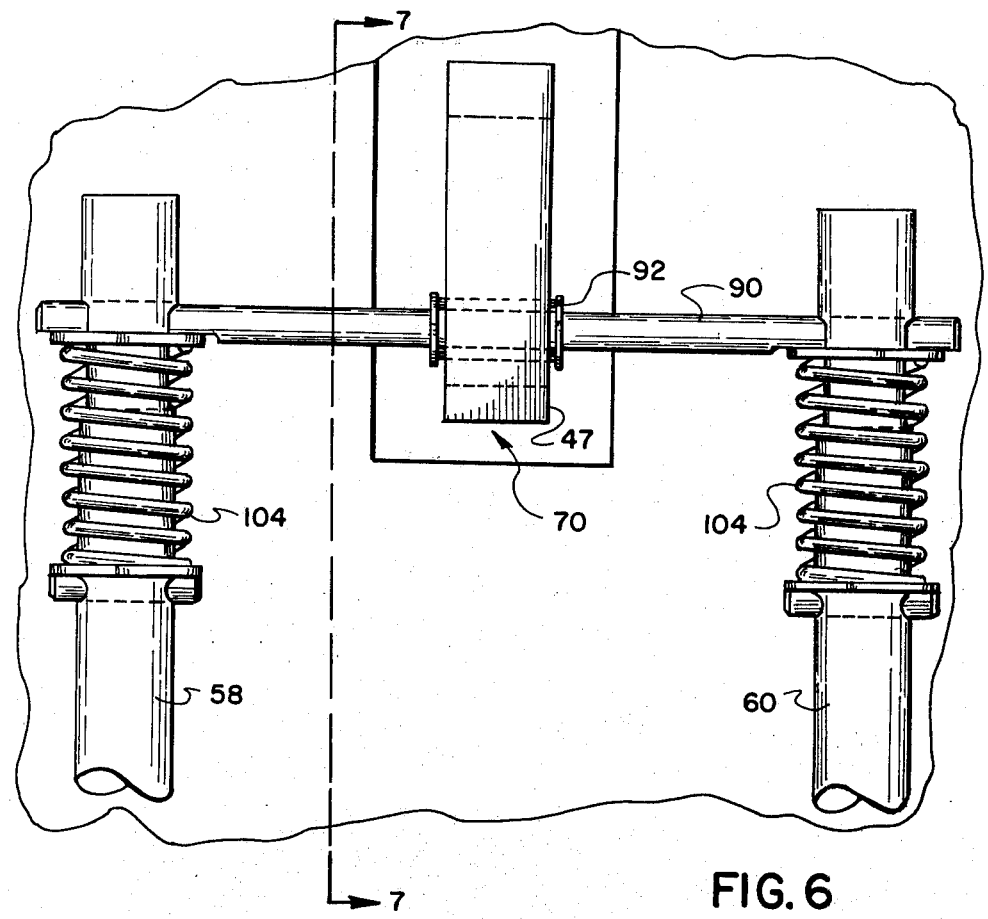
FIG. 6 is a fragmentary top plan view of the carriage and showing the position lock for the carriage.
Figure 7:
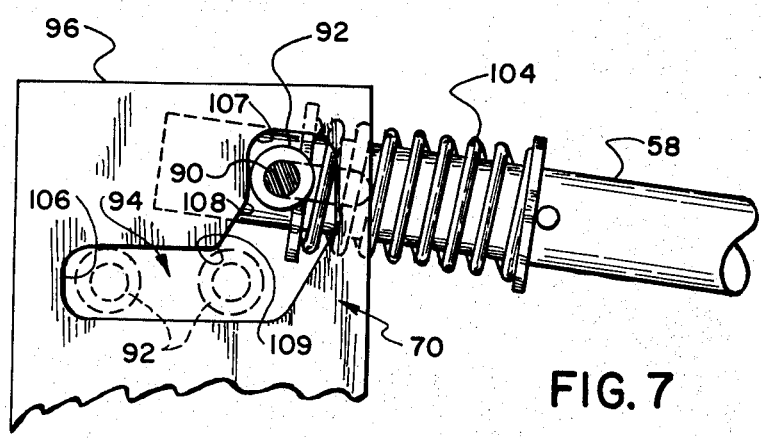
FIG. 7 is a sectional view of the position lock, taken along line 7—7 in FIG. 6.

Carriage 40 is adapted to be releasably held in a dispensing position by a position lock 70. As shown in FIGS. 6 and 7, position lock 70 comprises a pin 90 having a roller 92 thereon which is movable in a slot 94 located in an upper end 96 of counterbalance arm 47. Pin 90 is mounted in slots 100 in members 58, 60, and the pin 90 is movable in slots 100 against the bias of springs 104. With reference to FIG. 7, roller 92 is movable from the dotted-line position at end 106 of slot 94, when carriage 40 is in the transport position, to a second dotted-line position adjacent bend 109 in slot 94 when carriage 40 has reached the dispense position; additional downward movement of handle 56 will move roller 94 to end 107 of slot 94. In moving to end 107, roller 94 passes over a protrusion 108 in slot 94 which functions as an over-center device to prevent roller 92 from moving from end 107 and thereby releasably locking carriage 40 in a dispense position. Position lock 70 can be released by lifting up on handle 56 with sufficient force to contract springs 104 which permits roller 92 to move over protrusion 108 and to move to end 106 in slot 94.

As shown in FIG. 2, detent slots 74 are also provided adjacent an end 116 of track 50 to permit carriage 40 to be pivoted down to eject a used metering tip 76 into a waste receptacle 115 (FIG. 1), to pick up a new metering tip 76, and to aspirate fluid from sample cup 18.

In the operation of the disclosed invention, metering apparatus 12 would first be moved to a position to pick up a new tip 76, and then to a position to aspirate in a supply of sample fluid from a cup 18. Next, apparatus 12 would be moved to a position adjacent one of the channels 22. When a detent slot 74 is contacted by roller 48, the operator would press down on handle 56 to move roller 48 into slot 74 and pivot the carriage toward a test element 20 at a metering station. As the carriage 40 is moved downwardly, locating means 80 would engage the carriage to locate tip 76 precisely relative to element 20. Before starting the dispensing operation, handle 56 would be moved down far enough to lock the carriage in the dispense position; a dispense button 110 would then be depressed to deliver the fluid to a test element 20. When the metering operation is complete, carriage 40 is raised to a transport position, and the apparatus is moved to new channel 22 where the process is repeated.

As noted previously, there are certain advantages from having a manually-actuated analyzer for use under field and emergency conditions. The disclosed apparatus provides a novel and unique manually-operated mechanism for transporting and precisely locating a metering tip relative to a test element. The two locating means for carriage 40 function in sequence to locate the tip 76 at a metering station 21, with a minimum of effort on the part of the operator. The first locating means, which includes detent slots 74, serves to notify the operator when the carriage arrives at a channel 22 and to locate the carriage between predetermined limits. The second locating means, which is more precise than the first locating means, is operable after the carriage has been located within predetermined limits to provide the final precise positioning which is necessary to achieve the desired test results.

The invention has been described in detail with particular reference to preferred embodiments thereof, but it will be understood that variations and modifications can be effected within the spirit and scope of the invention.

What is claimed is:

1. In an analyzer for the chemical analysis of a sample fluid wherein metering apparatus is moved through a plurality of stations, said metering apparatus comprising dispensing means for delivering a predetermined amount of fluid to a substrate in each of said stations, the combination comprising:

a carriage for receiving said dispensing means;

means for supporting said carriage for movement along a path which passes through each of said stations; and means for positioning said carriage at each of said stations, said positioning means comprising first and second locating means at each station operable in sequence on said carriage to precisely locate said dispensing means relative to said substrate, said first locating means being operable on said carriage to locate the carriage along said path between predetermined limits and said second locating means being operable on said carriage after said first locating means to precisely locate said carriage along said path within said limits.

2. The combination, as recited in claim 1, wherein said carriage is pivotal between a transport position and a dispense position, said carriage is movable from station to station in said transport position and is adapted to deliver fluid to said substrate in the dispense position, said first locating means is operable on the carriage in said transport position and said second locating means is operable on the carriage in said dispense position.

3. The combination, as recited in claim 1, wherein said first locating means is operable in a horizontal plane, and said second locating means is operable in a horizontal plane and is adapted to define the spacing in a vertical direction between said dispensing means and said substrate.

4. The combination, as recited in claim 1, wherein said carriage comprises a first arm for supporting said dispensing means and a second arm at an angle to said first arm, said second arm having roller means thereon which cooperates with said positioning means.

5. The combination, as recited in claim 4, wherein said first locating means comprises track means for receiving said roller means.

6. The combination, as recited in claim 5, wherein said carriage comprises a counterbalance arm journalled on said shaft, said counterbalance arm comprising a second roller means received in said track means, and spring means connecting said second arm and said counterbalance arm.

7. The combination, as recited in claim 1, wherein said supporting means comprises a shaft extending through each of said stations, and said carriage is journalled on said shaft for both longitudinal and pivotal movement.

8. The combination, as recited in claim 1, wherein said positioning means includes means for preventing pivotal movement of said carriage except when the carriage is located at one of said stations.

9. In a multichannel analyzer for measuring the ionic activity of sample biological liquids deposited on a test element containing a pair of ion-selective electrodes, the combination comprising:

a metering station in each of the analyzer channels, each of said stations being constructed to receive a test element for performing an analysis;

metering apparatus movable to each of said stations, said apparatus including dispensing means for depositing a predetermined amount of fluid on a test element in each of said stations and a carriage for supporting said dispensing means;

support means for said carriage, said support means including a shaft which extends along said stations, said carriage being movable along said shaft and pivotal thereabout between a transport position and a dispense position; and means for positioning said carriage at each of said metering stations, said positioning means comprising detent means at each station for locating said carriage in said transport position between predetermined limits and second locating means at each station for locating said carriage in the dispense position within said limits and relative to a test element in a metering station.

10. The combination, as recited in claim 9, wherein said carriage comprises a pair of arms disposed generally perpendicular to each other, one of said arms supporting said dispensing means and the other arm being journalled on said support means.

11. The combination, as recited in claim 10, wherein said positioning means comprises track means having slots at each of said stations, and said other arm comprises first roller means operable in said track means and receivable in said slots.

12. The combination, as recited in claim 11, wherein said carriage comprises a counterbalance arm, and said counterbalance arm having roller means adapated to operate in said track means.

13. The combination, as recited in claim 12, wherein said other arm and said counterbalance arm are biased toward each other, and said carriage is pivotal from said transport position to said dispense position against said bias when said first roller means is received in said slots.

14. The combination, as recited in claim 13, wherein damper means connects said one arm and said counterbalance arm to regulate the speed at which said carriage can be pivoted.

15. Apparatus for depositing a predetermined amount of fluid on a test element at a plurality of stations in a chemical analyzer, said apparatus comprising:

means for dispensing fluid in precise amounts and for aspirating a supply of fluid from a sample cup;

carriage means for supporting said dispensing and aspirating means for movement to each of said stations;

support means for said carriage means, said support means comprising a shaft extending adjacent each of said stations, and said carriage means being pivotal about said shaft at each of said stations between a transport position and a dispense position, said carriage means having locking means for releasably holding the carriage in the dispense position and movable therealong; and means for positioning said carriage means at each of said stations, said positioning means comprising first locating means which is operable on said carriage means to locate said dispensing means between predetermined limits and second locating means which is operable on said carriage means for locating said dispensing means within said limits relative to a test element in a metering station.

* * * * *